(12) United States Patent
Burkholz et al.

(10) Patent No.: US 12,102,774 B2
(45) Date of Patent: Oct. 1, 2024

(54) VASCULAR ACCESS DEVICE ASSEMBLY FACILITATING SINGLE-HANDED PATENCY PROBE ADVANCEMENT

(71) Applicant: Becton, Dickinson and Company, Franklin Lakes, NJ (US)

(72) Inventors: Jonathan Karl Burkholz, Salt Lake City, UT (US); Bin Wang, Sandy, UT (US); Weston F. Harding, Lehi, UT (US); Curtis H. Blanchard, Herriman, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/225,442

(22) Filed: Jul. 24, 2023

(65) Prior Publication Data

US 2023/0364381 A1 Nov. 16, 2023

Related U.S. Application Data

(63) Continuation of application No. 17/195,337, filed on Mar. 8, 2021, now Pat. No. 11,744,984.

(Continued)

(51) Int. Cl.
*A61M 25/00* (2006.01)
*A61M 25/06* (2006.01)
*A61M 39/02* (2006.01)
*A61M 39/10* (2006.01)
*A61M 25/09* (2006.01)

(52) U.S. Cl.
CPC .... *A61M 25/0023* (2013.01); *A61M 25/0606* (2013.01); *A61M 25/0662* (2013.01); *A61M 39/02* (2013.01); *A61M 39/10* (2013.01); *A61M 2025/09116* (2013.01); *A61M 2039/0202* (2013.01)

(58) Field of Classification Search
CPC .......... A61M 25/0023; A61M 25/0606; A61M 25/0662; A61M 39/02; A61M 39/10; A61M 2025/09116; A61M 2039/0202
USPC .......................................................... 604/164
See application file for complete search history.

(56) References Cited

U.S. PATENT DOCUMENTS

2012/0277627 A1\* 11/2012 Devgon ........... A61B 5/150717
600/576
2021/0212618 A1 7/2021 Burkholz et al.

FOREIGN PATENT DOCUMENTS

WO 2011011436 A2 1/2011
WO 2012149109 A2 1/2012
(Continued)

*Primary Examiner* — Phillip A Gray
(74) *Attorney, Agent, or Firm* — The Webb Law Firm

(57) ABSTRACT

An IV device assembly may include a lumen forming a fluidic channel within the IV device assembly. The lumen may be fluidically coupled to a vascular access device (VAD) coupler via a funnel coupler, and an IV device assembly coupler at a proximal end of the lumen. The IV device assembly may also include one or more of the following: a collapsible sleeve formed coaxially around a first portion of the lumen and mechanically coupled to the funnel coupler, a patency instrument formed along a second portion of the lumen within the collapsible sleeve and into the VAD coupler, a translation handle that translates the patency instrument out of a distal end of the VAD coupler, and a fixed grip formed around the lumen to maintain a position of the IV device assembly relative to the translation handle.

19 Claims, 11 Drawing Sheets

Related U.S. Application Data

(60) Provisional application No. 62/993,405, filed on Mar. 23, 2020.

(56) References Cited

FOREIGN PATENT DOCUMENTS

| | | |
|---|---|---|
| WO | 2014153508 A1 | 9/2014 |
| WO | 2020014149 A1 | 1/2020 |
| WO | 2021141765 A1 | 7/2021 |

* cited by examiner

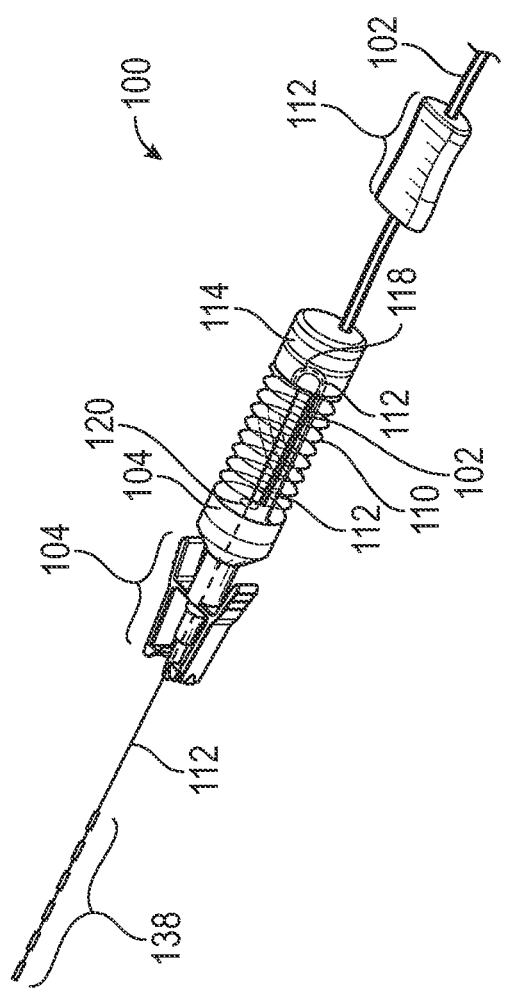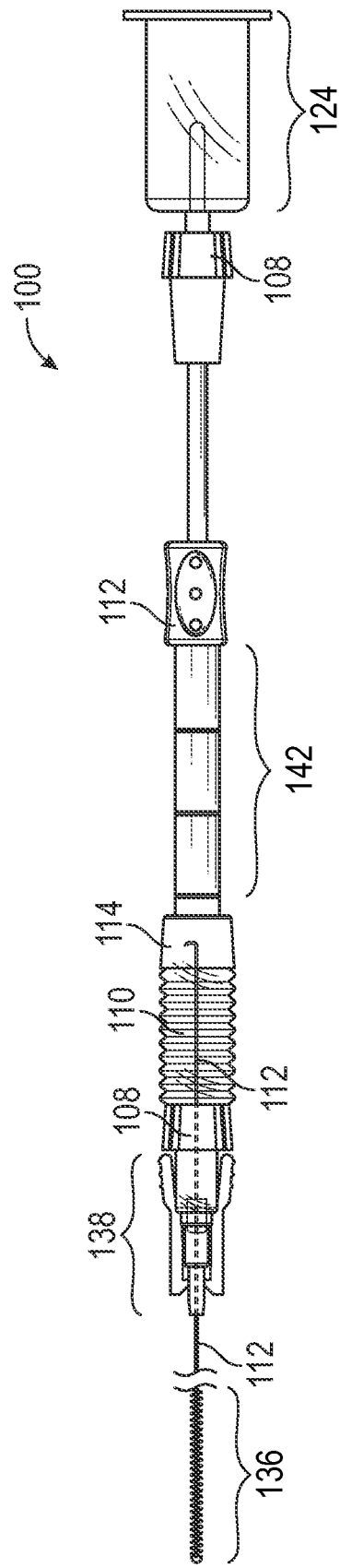
FIG. 5
FIG. 6

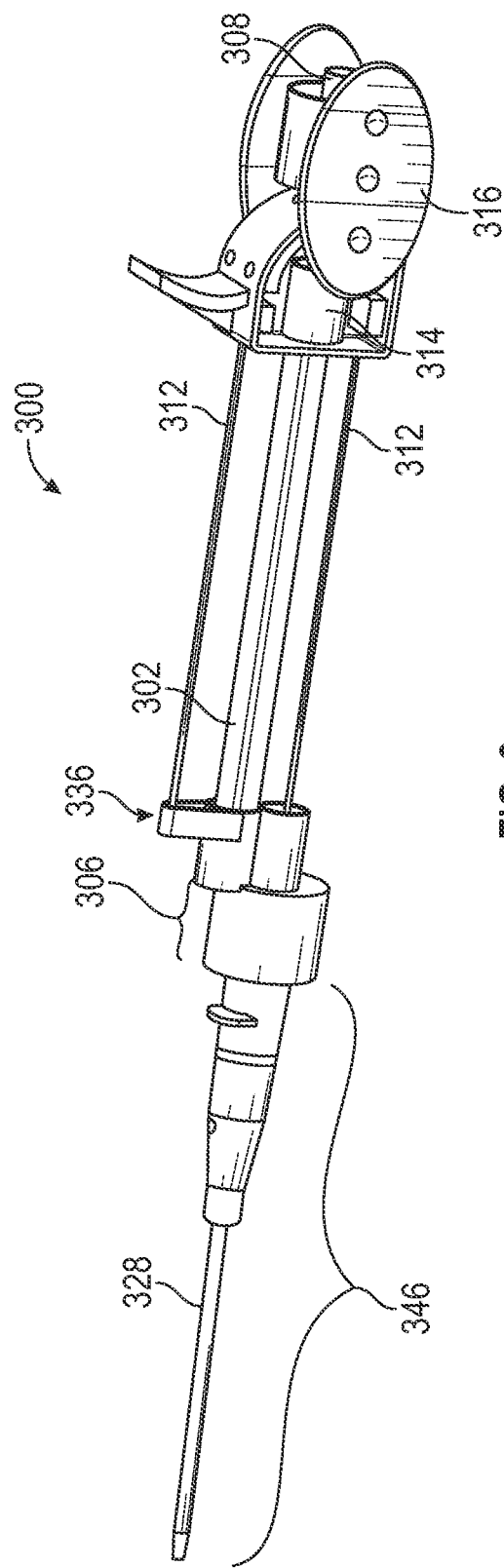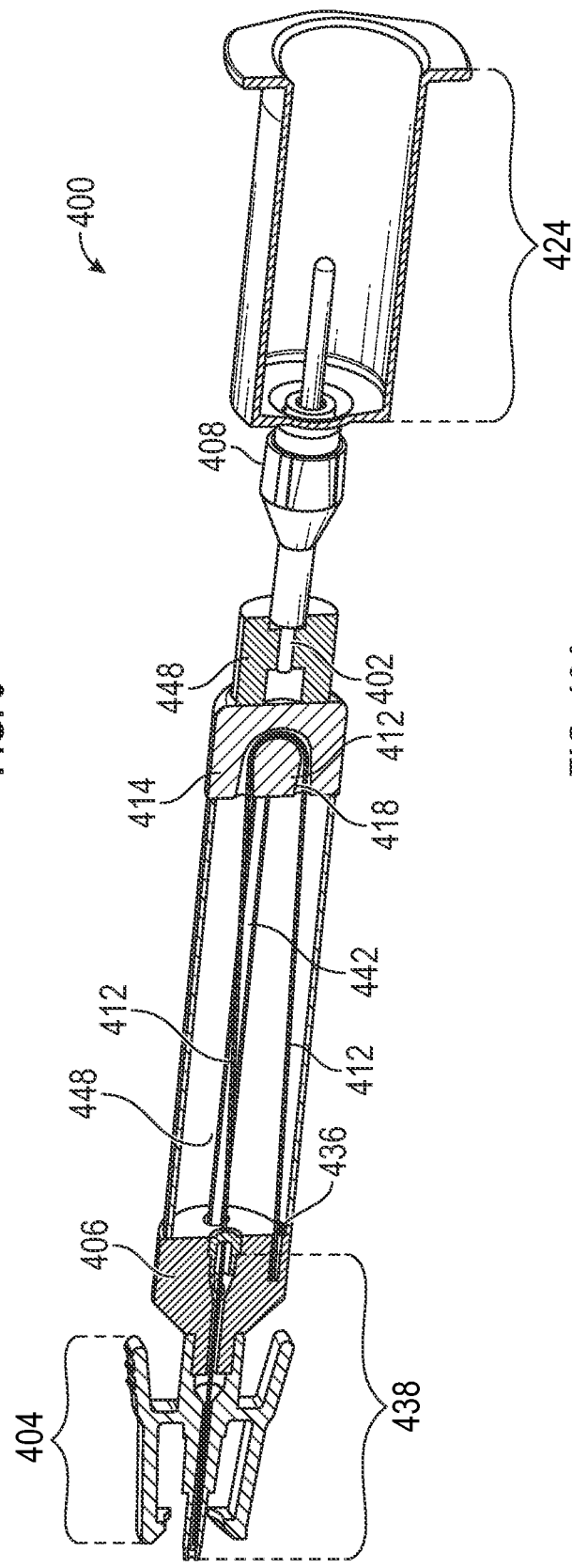

VASCULAR ACCESS DEVICE ASSEMBLY FACILITATING SINGLE-HANDED PATENCY PROBE ADVANCEMENT

CROSS-REFERENCE TO RELATED APPLICATIONS

This application is a continuation of U.S. patent application Ser. No. 17/195,337, filed on Mar. 8, 2021, entitled "Vascular Access Device Assembly Facilitating Single-Handed Patency Probe Advancement", which claims the benefit of U.S. Provisional Patent Application No. 62/993,405, filed on Mar. 23, 2020, entitled "Vascular Access Device Assembly Facilitating Single-Handed Patency Probe Advancement," the disclosures of which are incorporated herein in their entirety.

BACKGROUND

Extending the patency of an intravenous (IV) device may improve the viability of a long-term placement and reduce the need to subject the patient to the expense and trauma of unnecessary additional intervention procedures. In further detail, during use of an IV device, the IV device is inserted into the patient's blood vessel and, in some instances, a needle is pulled out of the IV device while the IV device remains within the patient's blood vessel. In some circumstances, the IV device is left to remain in the patient's blood vessel for up to 30 days. This is done so as to allow a clinician or other health care provider (HCP) to have fluidic access to the patient's blood stream during care. This continuous fluid access to the patient's blood stream allows a clinician or other HCP to, when appropriate, draw one or more blood samples or administer one or more infusing fluids, such as a saline solution, various medicaments, and total parenteral nutrition.

The patency of the IV device may be compromised, however, while the IV device is within the patient's blood vessel. Any blockage may persist and cause the IV device to fail necessitating another administration of an IV device into the patient's body. This may increase the trauma felt by the patient and lead to other medical issues such as inflammation of the blood vessel among other medical issues.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to an intravenous (IV) device assembly used to interface with, for example, a vascular access device (VAD) such as a catheter. In some embodiments, the IV device assembly may provide for a fluidic path to the VAD device while also providing for a patency instrument used to periodically check the patency of the VAD while a needle and/or the catheter is within a patient's blood vessel.

The IV device assembly may include a lumen forming a fluidic channel within the IV device assembly, the lumen fluidically coupled to a VAD coupler at a distal end via a funnel coupler and an IV device assembly coupler at a proximal end of the lumen. In these embodiments, the IV device assembly may further include a collapsible sleeve formed coaxially around a first portion of the lumen and mechanically coupled to the funnel coupler. In these embodiments, the IV device assembly may further include a patency instrument formed along a second portion of the lumen within the collapsible sleeve and into the VAD coupler with a translation handle to translate the patency instrument out of a distal end of the VAD coupler and a fixed grip formed around the lumen to maintain a position of the IV device assembly relative to the translation handle. In these embodiments, the patency instrument may a double-length patency instrument or a single length patency instrument.

In the embodiment where the patency instrument is a double length patency instrument, a first end of the patency instrument may be mechanically coupled to the funnel coupler and passed through a channel formed in the translation handle so that the patency instrument may be routed through a seal formed in the funnel coupler and into the VAD coupler. In these embodiments, when the translation handle is moved distally towards the VAD coupler, the patency instrument may be extended past the VAD coupler and, in some embodiments, enter the catheter, for example, so that the patency instrument may check the patency of the catheter. Similarly, where the IV device assembly includes a single-length patency instrument, the first end of the patency instrument is anchored on the translation handle and translation of the translation handle towards a distal end of the IV device assembly thereby extending the patency instrument beyond the VAD coupler as described.

In some embodiments, the lumen used to for the fluidic path through the IV device assembly may be offset from a central longitudinal axis. In these embodiments, the patency instrument may enter the funnel coupler at a central longitudinal axis so that the passage of the patency instrument through the funnel coupler. Additionally, because the lumen is offset from the fluid axis of the VAD coupler to which the funnel coupler is mechanically coupled to, the funnel coupler may include a coupler channel to complete a fluidic channel from the lumen to the VAD coupler.

In some embodiments, the IV device assembly may include a catheter, such as, for example, a peripheral IV catheter (PIVC) or another suitable catheter, coupled to the VAD coupler. In some embodiments, the catheter may include a needle to access a blood vessel of a patient. In some embodiments, the IV device assembly further includes a blood sample access device mechanically coupled to the IV device assembly coupler to receive a blood sample via the IV device assembly.

In some embodiments, the patency instrument may include a guidewire that comprises a porous distal end. In a specific example, the porous distal end may include a winding of material around a central portion of the patency guidewire.

In some embodiments, the collapsible sleeve includes a coil spring formed therein. The coil spring may be biased to extend the translation handle towards a proximal end of the IV device assembly. In some embodiments, the coil spring extends the translation grip to abut against the fixed grip.

The specification describes an IV device assembly that includes a lumen forming a fluidic channel within the IV device assembly, the lumen fluidically coupled to a vascular access device (VAD) coupler at a distal end via a funnel coupler; and an IV device assembly coupler at a proximal end of the lumen; a patency instrument formed along a length of the lumen, wherein a first end of the patency instrument is mechanically coupled to the funnel coupler; a translation handle to translate the patency instrument out of a distal end of the VAD coupler, wherein the patency instrument passes through a channel formed in the translation handle and passes down and into the VAD coupler; and a fixed grip formed around the lumen to maintain a position of the IV device assembly relative to the translation handle. In these embodiments, the IV device assembly may include a collapsible sleeve formed coaxially around a first portion of the lumen and mechanically coupled to the funnel coupler. In some embodiments, the lumen may be offset from a fluid axis of the VAD coupler.

In some embodiments, the IV device assembly may include the catheter coupled to the VAD coupler, the catheter including a needle to access a blood vessel of a patient and a blood sample access device mechanically coupled to the IV device assembly coupler to receive a blood sample via the IV device assembly. In some embodiments, the patency instrument may include a guidewire coupled to a porous distal end formed at an end of the patency instrument.

The present disclosure further describes an IV device assembly that includes a lumen forming a fluidic channel within the IV device assembly, the lumen fluidically coupled to: a vascular access device (VAD) coupler at a distal end via a funnel coupler; and an IV device assembly coupler at a proximal end of the lumen; a patency instrument formed along a length of the lumen and into the VAD coupler; a translation handle to translate the patency instrument out of a distal end of the VAD coupler, wherein a first end of the patency instrument is mechanically coupled to the translation handle; and a fixed grip formed around the lumen to maintain a position of the IV device assembly relative to the translation handle. In these embodiments, the IV device assembly may further include the catheter coupled to the VAD coupler. In these embodiments, the lumen of the IV device assembly is offset from a fluid axis of the VAD coupler. In these embodiments, the patency instrument is a guidewire that comprises a porous second end. In these embodiments, the IV device assembly may include a collapsible sleeve formed coaxially around a first portion of the lumen and mechanically coupled to the funnel coupler. In these embodiments, the collapsible sleeve further includes a coil spring that creates a space between the lumen and bias the translation handle towards a proximal end of the IV device assembly.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 5 a perspective view of an IV device assembly, according to some embodiments of the present disclosure;

FIG. 6 is a front elevation view of an IV device assembly, according to some embodiments of the present disclosure;

FIG. 9 is a perspective view of an IV device assembly, according to some embodiments of the present disclosure;

FIG. 10A is perspective, section view of a rigid or semi-rigid IV device assembly, according to some embodiments of the present disclosure;

DESCRIPTION OF EMBODIMENTS

Figure 1:
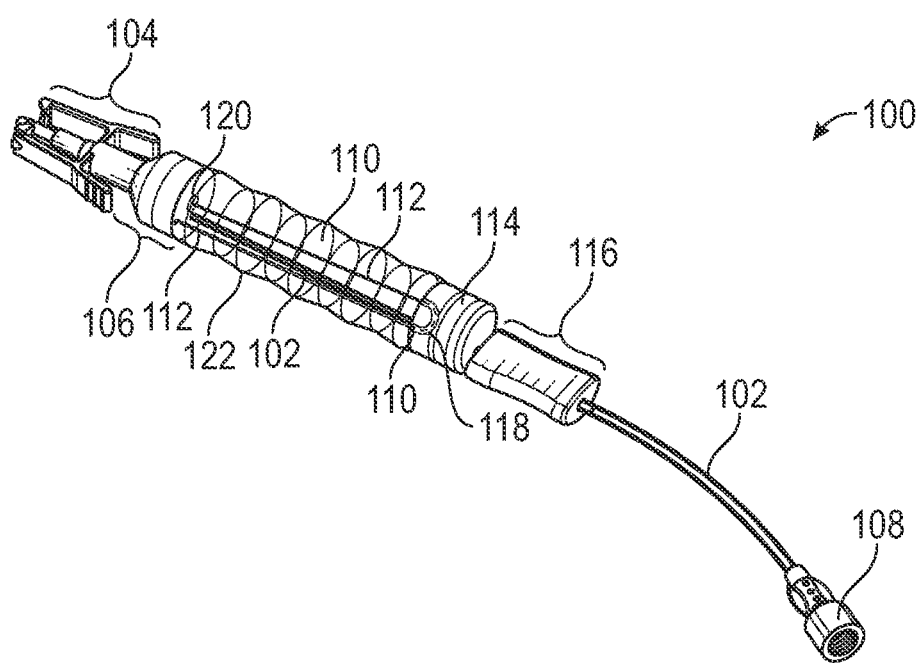
FIG. 1 is a perspective view of an intravenous (IV) device assembly, according to some embodiments of the present disclosure.

FIG. 1 is a perspective view of an IV device assembly 100 according to some embodiments of the present disclosure. In some embodiments, the IV device assembly 100 may be mechanically and fluidically coupled to a vascular access device (VAD) such as a catheter coupled to the VAD coupler 104. In these embodiments, the VAD may include a needle, a catheter, or a combination of a needle and catheter used to access a blood vessel of a patient. In the embodiment where the VAD includes a needle and a catheter, the needle may be removed from within the catheter once the VAD has been inserted into the patient's blood vessel. In these embodiments, the catheter may remain within the blood vessel and, as described in the present disclosure may be subjected to a patency check using the patency instrument 112 described in the present disclosure. In some embodiments, the catheter may include a peripheral IV catheter (PIVC), a peripherally-inserted central catheter (PICC), or a midline catheter. In the embodiment where the VAD includes a needle, the patency instrument 112 may also be used to check the patency of the needle.

In some embodiments, the IV device assembly 100 may be mechanically and fluidically coupled to a blood sample access device. In some embodiments, the blood sample access device may be mechanically coupled to the IV device assembly coupler 108 to receive a blood sample via the IV device assembly 100. In some embodiments, the blood sample access device may include a BD VACUTAINER® LUER-LOK™ Access Device produced by Becton, Dickinson and Company of Franklin Lakes, New Jersey, or another suitable blood sample access device.

In some embodiments, the IV device assembly 100 may include a lumen 102 that is fluidically coupled to the VAD coupler 104 via a funnel coupler 106 at a distal end of the IV device assembly 100. In these embodiments, the funnel coupler 106 may include funnel coupler channel that completes a fluid channel between the lumen 102 and the fluid channel formed within the VAD coupler 104. In some embodiments, the lumen 102 may be offset from the fluid channel formed in the VAD coupler 104. In these embodiments, the lumen 102 may be offset from the fluid pathway of the VAD coupler 104 because the longitudinal axis of the fluid pathway through the VAD coupler 104 is not the same as the longitudinal axis of the fluid pathway of the lumen 102 at the location where the lumen 102 is fluidically coupled to the funnel coupler 106. This offset of fluidic channels will be further described and is illustrated in connection with FIG. 3. In some embodiments, the gauge of the lumen 102 may be optimized to minimize hemolysis and provides adequate flow rate for receiving blood samples. In some embodiments, the lumen 102 may be made of polyvinyl chloride (PVC), thermoplastic elastomer (TPE), thermoplastic polyurethane (TPU), or other medical-grade tubing material. As described in the present disclosure, in some embodiments, the lumen 102 may include markings formed thereon that describes the position or extension of the patency instrument 112 during use of the IV device assembly 100.

In some embodiments, the IV device assembly 100 may further include a collapsible sleeve 110 formed coaxially around a first portion of the lumen 102 and mechanically coupled to the funnel coupler 106. In some embodiments, the collapsible sleeve 110 may be mechanically coupled to the funnel coupler 106 via, for example, using an adhesive or by implementing an ultrasonic welding process. In some embodiments, the collapsible sleeve 110 may be made of a foldable and pliant material that allows the collapsible sleeve 110 to be collapsed in on itself.

In some embodiments, a proximal end of the collapsible sleeve 110 may be mechanically coupled to a translation handle 114. In some embodiments, the collapsible sleeve 110 may be mechanically coupled to the translation handle 114 via, for example, using an adhesive or by implementing an ultrasonic welding process. In some embodiments, during operation, the translation handle 114 may be allowed to move along a longitudinal axis of the lumen 102 such that the collapsible sleeve 110 may be folded against the funnel coupler 106.

In some embodiments, the collapsible sleeve 110 may be made of an elastomeric or polymer film. The elastomeric or polymer film may allow the collapsible sleeve 110 to be collapsed in on itself and returned to its non-collapsed state without damage to the elastomeric or polymer film itself. In some embodiments, the collapsible sleeve 110 may include a coiled spring 122 formed therein to cause the collapsible sleeve 110 to be extended (e.g., as illustrated in FIG. 1) when a force is not applied to the translation handle 114 towards a distal end of the IV device assembly 100. In some embodiments, the coiled spring 122 may be biased to return to the non-deployed states as illustrated in FIG. 1. In some embodiments, the collapsible sleeve 110 may be semi or fully transparent so as to allow a clinician or other HCP to view the lumen 102 and/or any measurement markings placed on the lumen 102.

In some embodiments, the IV device assembly 100 may include a grip 116. In some embodiments, the grip 116 may be any body that is fixed and formed around the lumen 102 to maintain the position of the IV device assembly 100 relative to the translation handle 114. In some embodiments, during operation of the IV device assembly 100, a clinician may grasp the grip 116 with one hand or multiple fingers and translate the translation handle 114 along the length of the translation handle 114 towards a distal end of the IV device assembly 100 with another hand or other fingers. In some embodiments, the ergonomics that define the shape of the grip 116 may be such that the grip 116 and translation handle 114 is operated with a single hand.

In some embodiments, the patency instrument 112 may be about double the length of the collapsible sleeve 110. In these embodiments, a first end of the patency instrument 112 is anchored to the funnel coupler 106. The patency instrument 112 may then be passed through a channel 118 formed within the translation handle 114. The patency instrument 112 may then be passed back towards the funnel coupler 106 and through a bore formed through the funnel coupler 106 and into a fluid channel formed in the VAD coupler 104. In some embodiments, because the patency instrument 112 may enter into the fluid channel formed in the VAD coupler 104, the interface between the fluid channel formed in the VAD coupler 104 and the bore formed in the funnel coupler 106 for the patency instrument 112 may include a seal (not illustrated). The seal may prevent fluids such as blood and infusing fluids, such as a saline solution, various medicaments, and total parenteral nutrition from exiting the funnel coupler 106 and passing into the collapsible sleeve 110.

In some embodiments, the patency instrument 112 may include an instrument that advances into the blood vessel of the patient to provide improved patency. In some embodiments, the instrument may be atraumatic. In some embodiments, the patency instrument 112 may include a guidewire that is flexible enough to pass through the fluidic channels described in the present disclosure while still being resilient enough to dislodge materials within the VAD.

In some embodiments, the IV device assembly 100 may improve the patency of a VAD mechanically and fluidically coupled to the VAD coupler 104 for fluid delivery and sampling as described in the present disclosure. In some embodiments, because the IV device assembly 100 is mechanically coupled to the VAD inserted into a patient's body, the IV device assembly 100 may be selectively removed from and coupled to the VAD when the patency of the VAD is to be checked. In some embodiments, the VAD may include a separate port used to provide medicaments to the patient's body as well as receipt of a blood sample. In some embodiments, the IV device assembly 100 may be coupled to the VAD so long as the VAD is inserted into the patient's body. In some embodiments, the VAD may include a catheter with a needless access connector (NAC) attached near a patient access point on the catheter. In these embodiments, the patency instrument 112 may be sufficiently stiff yet flexible to bend as it advances from the VAD coupler 104 and enters the VAD. In some embodiments, the IV device assembly 100 may be used to deliver an instrument into the VAD or the patient's vein such as a sensor that monitors patient vitals. In these embodiments, an end of the patency instrument 112 may be mounted with this sensor.

The VAD coupler 104 illustrated in FIG. 1 is depicted as a blunt cannula snap-type connector, according to some embodiments. However, the present disclosure contemplates that other types of connectors may be used. In an alternative embodiment, the IV device assembly 100 may include a threaded male luer connector, a clip luer connector, a threaded male luer connector with a removably attached blunt cannula snap connector, or any other type of connector that mechanically and fluidically couples the IV device assembly 100 to a VAD as described in the present disclosure.

In some embodiments, the IV device assembly 100 may provide for an integrated extension set with optimized fluid resistance and a patency improving via the patency instrument 112 that is relatively less traumatic on the patient's vein. In some embodiments, the IV device assembly 100 may be used by a single hand of the clinician allowing for the clinician to have a free hand. In some embodiments, the IV device assembly 100 may be compact and include the extension set in the form of a lumen 102 that may be coupled to a blood sample access device to access a blood sample. In some embodiments, the IV device assembly 100 may also eliminate a rigid housing and remain flexible in order to reduce the likelihood of VAD complications when the VAD is inserted into the patient's vein. Through the use of the IV device assembly 100, the workflow may be streamlined and steps may be reduced by having the IV device assembly 100 coupled to a VAD that fulfills multiple purposes. Medical waste may also be reduced through use of the IV device assembly 100 because the IV device assembly 100 includes fewer and smaller components. With the reduction in size of the IV device assembly 100, the IV device assembly 100 may more easily fit within a sharps container or medical waste receptacle.

Figure 2:
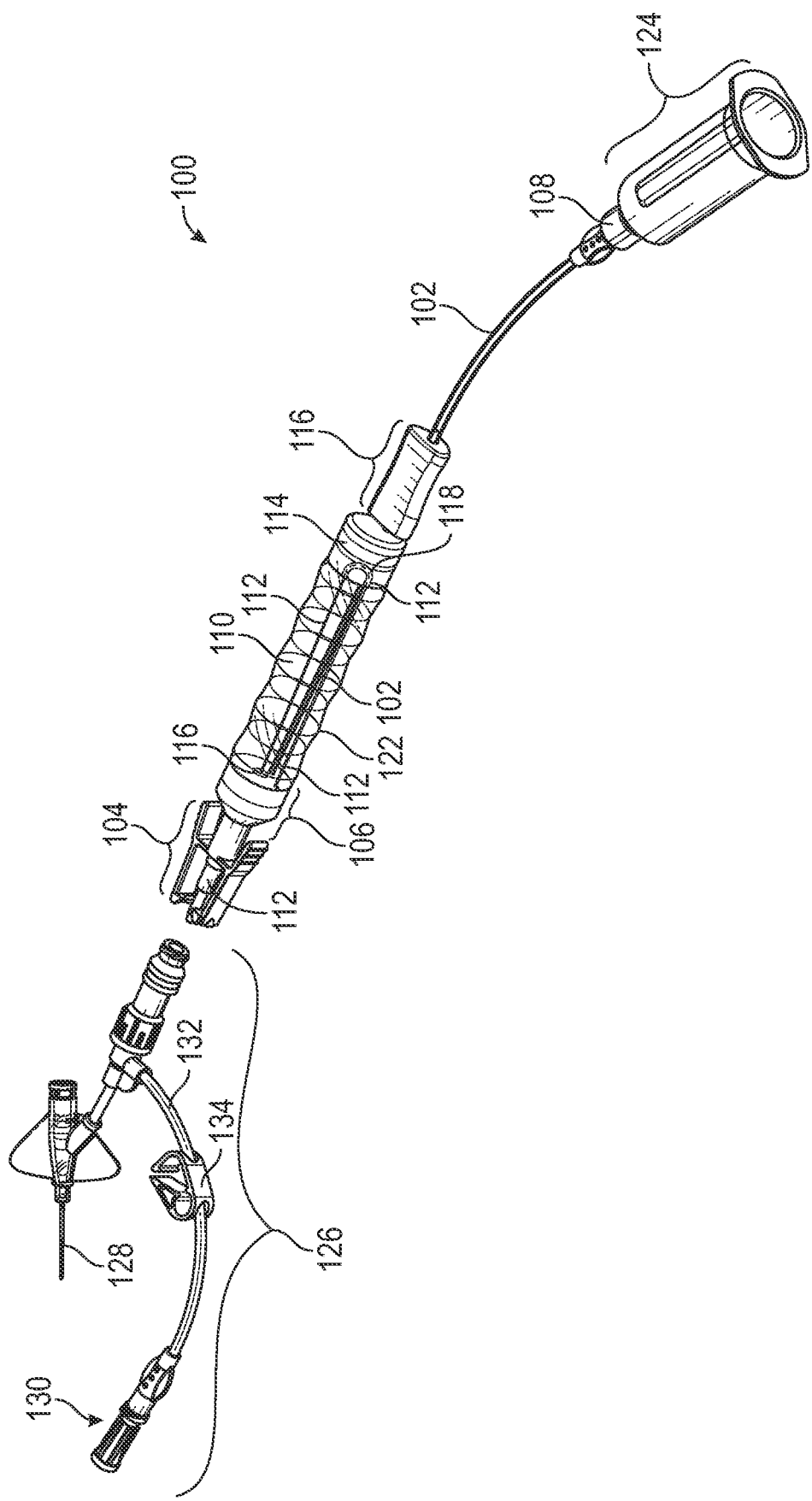
FIG. 2 is a perspective view of an IV device assembly, according to some embodiments of the present disclosure.

FIG. 2 is a perspective view of an IV device assembly 100 according to some embodiments of the present disclosure. FIG. 2 specifically illustrates the IV device assembly 100 along with a catheter 126 configured to couple to the VAD coupler 104 and a blood sample access device 124 coupled to the IV device assembly 100 via the IV device assembly coupler 108, according to some embodiments. Although FIG. 2 illustrates that the catheter 126 and blood sample access device 124 are coupled to the IV device assembly 100, the present disclosure contemplates that the IV device assembly 100 may be coupled to any type of device that would benefit from the functionalities provided by the IV device assembly 100.

In some embodiments, the IV device assembly 100 may be coupled to a blood sample access device 124 via the IV device assembly coupler 108 at the proximal end of the IV device assembly 100. In some embodiments, the blood sample access device 124 may be any type of device that may selectively allow for the receipt of a blood sample from the catheter 126 and IV device assembly 100. The blood sample access device 124 may, in some embodiments, be a BD VACUTAINER® LUER-LOK™ Access Device produced by Becton, Dickinson and Company of Franklin Lakes, New Jersey. In some embodiments, the blood sample access device 124 may be coupled to the IV device assembly coupler 108 via threading formed within the IV device assembly coupler 108 and on the blood sample access device 124. In some embodiments, during operation, the clinician may retrieve a blood sample by inserting a blood vial into the blood sample access device 124 where a need within the blood sample access device 124 punctures a septum on the blood vial and allows blood to flow from the lumen 102 and into the blood vial. In some embodiments, the blood sample access device 124 may include a valve that allows for the flow of blood therein only as a blood vial is inserted into the blood sample access device 124.

Also illustrated in FIG. 2 is a catheter 126, according to some embodiments. The catheter 126 is illustrated to be disconnected from the VAD coupler 104 of the IV device assembly 100. However, it is appreciated that, during use of the IV device assembly 100, the IV device assembly 100 may be coupled to the catheter 126 in order to allow the fluidic path to be coupled to the IV device assembly 100. In some embodiments, a catheter assembly 128 may include the catheter 126. In some embodiments, the catheter assembly 128 may include a needle and a catheter formed coaxially around the needle. During operation, the needle of the catheter assembly 128 may be removed so as to leave the catheter in the patient's body for fluid transfer.

In some embodiments, the catheter 126 may also include a port tubing 132 and port 130. In some embodiments, the port tubing 132 and port 130 may be used as a separate access point for the clinician to introduce an infusing fluid, such as a saline solution, various medicaments, and total parenteral nutrition into the blood vessel of the patient's body. In some embodiments, in order to prevent backflow of blood into the port tubing 132 and port 130, the port tubing 132 may include a port clamp 134. In some embodiments, the port clamp 134 may be clamped when the port 130 is not in use so that pressure within the port tubing 132 to prevent flow of blood therein.

Figure 3:
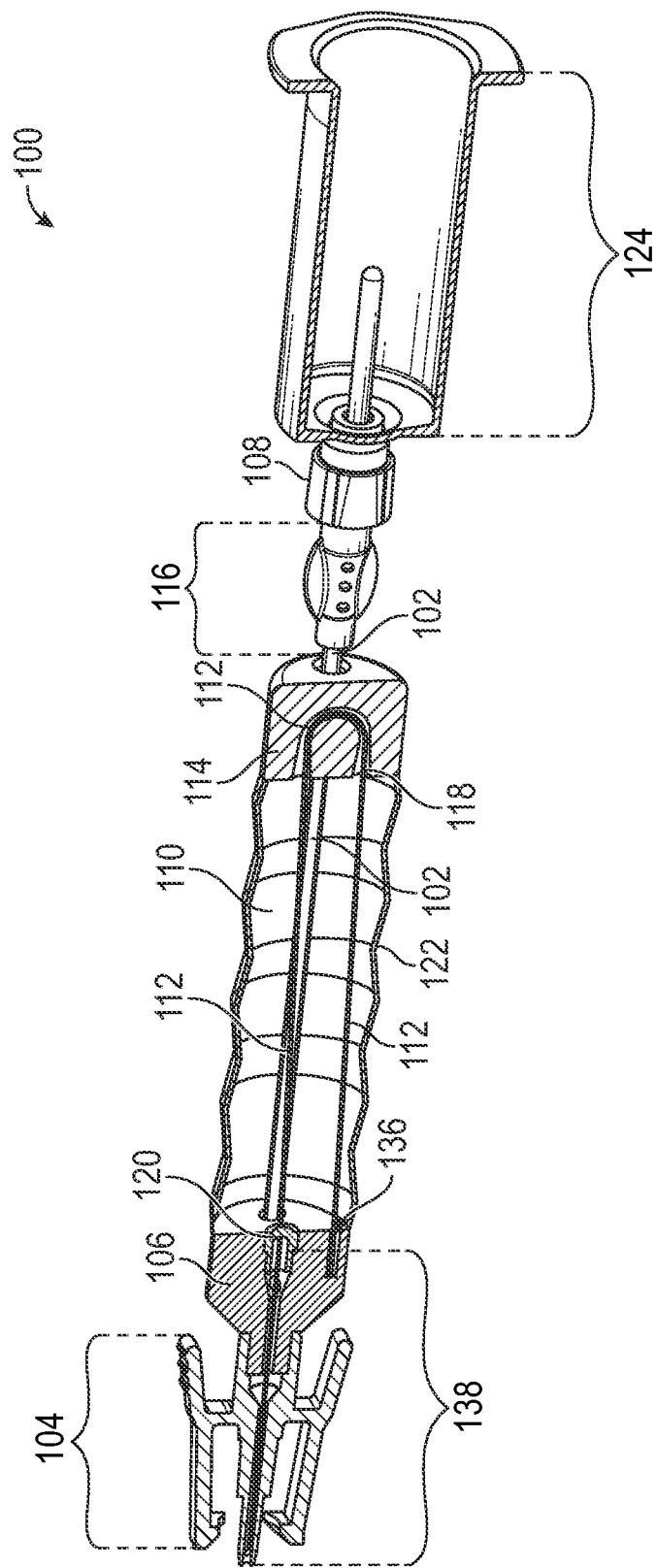
FIG. 3 is a perspective, section view of an IV device assembly, according to some embodiments of the present disclosure.

FIG. 3 is a perspective, section view of an IV device assembly 100 according to some embodiments of the present disclosure. FIG. 3 illustrates the IV device assembly 100 mechanically and fluidically coupled to a blood sample access device 124, according to some embodiments. The section view of the IV device assembly 100 illustrates that the patency instrument 112 may be a double passing patency instrument such that the distance a distal end of the patency instrument 112 moves may be about double the length of the collapsible sleeve 110.

In some embodiments, the patency instrument 112 may be anchored to the funnel coupler 106 at a patency instrument anchor 136. In these embodiments, the patency instrument anchor 136 may be a hole formed into the funnel coupler 106 with a first end of the patency instrument 112 fixed into the patency instrument anchor 136 and held therein by, for example, an adhesive or a mechanical coupling device. The patency instrument 112 may then be passed through a channel 118 formed in the translation handle 114. The channel 118 may be formed so that a length of the patency instrument 112 may easily pass through the channel 118 so that the patency instrument 112 may be moved out of the IV device assembly 100. After the patency instrument 112 is passed through the channel 118, the patency instrument 112 may be passed into the VAD coupler 104 and funnel coupler 106.

In some embodiments, the fluidic path of the lumen 102 may be offset from the fluidic path of the VAD coupler 104 such that the fluidic path of the lumen 102 is not the same as the mechanical path of the patency instrument 112 as it enters the funnel coupler 106. In some embodiments, the mechanical port at the funnel coupler 106 occupied by the patency instrument 112 may be coupled to the fluidic path of the VAD coupler 104 and lumen 102. In some embodiments, the mechanical port may include a seal 120 that seals the mechanical port for the patency instrument 112 from leaking fluids out of the fluidic paths of the VAD coupler 104 and funnel coupler 106.

In some embodiments, during operation of the IV device assembly 100, the clinician or other HCP may translate the translation handle 114 towards a distal end of the IV device assembly 100. In doing this, the patency instrument 112 may be forced out of the VAD coupler 104. In some embodiments, additionally, as the translation handle 114 is moved to a distal end of the IV device assembly 100, the patency instrument 112 may be passed through the channel 118 and through the funnel coupler 106. In some embodiments, because the first end of the patency instrument 112 is anchored at patency instrument anchor 136 and passed through the channel 118, the patency instrument 112 may be extended out of the VAD coupler 104 by approximately double the length of the distance between the translation handle 114 and the funnel coupler 106.

Figure 4:
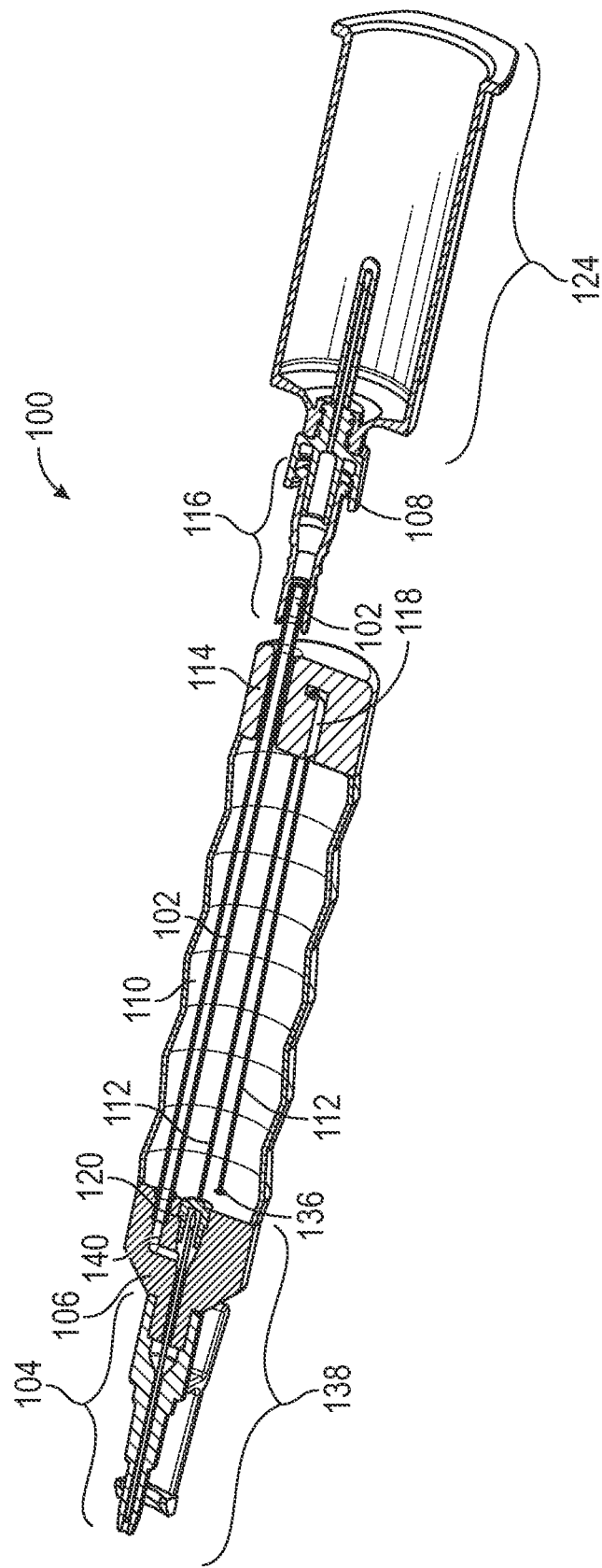
FIG. 4 is a perspective, section view of an IV device assembly, according to some embodiments of the present disclosure.

FIG. 4 is a perspective, section view of an IV device assembly 100 according to some embodiments of the present disclosure. The section view of FIG. 4 is similar to that illustrated in FIG. 3 except that the IV device assembly 100 has been rotated about a longitudinal axis by about 90 degrees, according to some embodiments.

As illustrated, for example in FIG. 4, a funnel coupler channel 140 may be formed through the funnel coupler 106. In some embodiments, the fluid channel of the lumen 102 is formed at the funnel coupler 106 at a location offset from the fluidic channel of the VAD coupler 104. In some embodiments, in order to fluidically couple the lumen 102 to the fluidic channel formed through the VAD coupler 104, the funnel coupler 106 may have a funnel coupler channel 140 formed therethrough in order to fluidically connect these two fluidic paths.

Again, during operation of the IV device assembly 100, the clinician or other HCP may translate the translation handle 114 towards a distal end of the IV device assembly 100. In doing this, the patency instrument 112 may be forced out of the VAD coupler 104. Additionally, as the translation handle 114 is moved to a distal end of the IV device assembly 100, the patency instrument 112 may be passed through the channel 118 and through the funnel coupler 106. Because the first end of the patency instrument 112 is anchored at patency instrument anchor 136 and passed through the channel 118, the patency instrument 112 may be extended out of the VAD coupler 104 by approximately double the length of the distance between the translation handle 114 and the funnel coupler 106. In some embodiments, fluid may be allowed to flow through the lumen 102, the funnel coupler channel 140, and the VAD coupler 104 when the patency instrument 112 is extended beyond the VAD coupler 104 and the translation handle 114 is translated towards the distal end of the IV device assembly 100. In some embodiments, the fluid may not be allowed to flow until the patency instrument 112 is in its retracted position illustrated in FIG. 4.

FIG. 4 further illustrates a distal end of the patency instrument 112 as being a porous distal end 138, according to some embodiments. In some embodiments, the porous distal end 138 may be made porous by, in some embodiments, coupling a spring winding around the distal end of the guidewire that forms the patency instrument 112. In some embodiments, the spring winding may be in the form of a fixed coil, a variable coil, a repeating variable coil, and open-ended extended coil, among other configurations. In some embodiments, the spring winding of the porous distal end 138 may be capped with a knob. In some embodiments, the length of the porous distal end 138 may vary and may be as long as or shorter than the distance between a distal end of the fluidic channel formed in the VAD coupler 104 to the distal end of the seal 220. In these embodiments, the diameter of the bore through the seal 220 may be smaller than the diameter of the porous distal end 138 and the porous distal end 138 may be prevented from entering the bore formed through the seal 220.

In some embodiments, a length of the lumen 102 may be selected based on one or more of the following: a gauge of a particular VAD, a particular VAD assembly configuration, or a clinical setup. In some embodiments, the lumen 102 may include a length L from the grip 116 to the funnel coupler 106. In some embodiments, the lumen 102 may include an inner diameter D.

Fluid flow in a fluid pathway through the lumen 102 can be analyzed using Poiseuille's equation when the lumen 102 is tubular:

$$Q = \frac{\pi D^4 \Delta P}{128 \mu L} = \frac{\Delta P}{R_f}$$

where $\Delta P$ is a change in pressure gradient across the length of the fluid pathway, D and L are the inner diameter and length, respectively, of the fluid pathway, $\mu$ is the viscosity of a fluid, and $$R_f = \frac{128 \mu L}{\pi D^4}$$

is the fluid resistance. Since $\mu$ is the viscosity of the fluid and not part of the extension tube geometry, a geometric factor $G_f$ is defined such that $R_f$ (the fluid resistance) is $$R_f = \frac{128 \mu}{\pi} G_f, \text{ where } G_f = \frac{L}{D^4}.$$

In some embodiments, the lumen 102 may have multiple sections with lengths (L1, L2, L3) and inner diameters of (D1, D2, D3), the geometric factor is then:

$$G_f = \frac{L1}{D1^4} + \frac{L2}{D2^4} + \frac{L3}{D3^4}$$

In some embodiments, the lumen 102 may have an inner diameter that changes over the length of the lumen 102, the geometric factor is then:

$$G_f = \int_0^L \frac{dl}{D(l)^4}$$

In some embodiments, the lumen 102 may have a cross section that is not circular or may have a complicated inner diameter profile. The geometric factor can then be determined by measuring the flow rate (Q) at given pressure ($\Delta P$) with known viscosity ($\mu$) fluid:

$$G_f = \frac{\pi \Delta P}{128 \mu Q}$$

The $G_f$ value of the lumen 102 may be selected to reduce the maximum shear stress for each VAD gauge to be the same or less than the max shear stress of a BD 21G VACUTAINER® UltraTouch™ push button blood collection set (available from Becton, Dickinson & Company of Franklin Lakes, New Jersey), which was previously considered the gold standard for blood draws. In some embodiments, $G_f$ value of the lumen 102 may be selected to reduce the maximum shear stress for each VAD gauge to be the same or less than the max shear stress of a BD 25G VACUTAINER® UltraTouch™ push button blood collection set (available from Becton, Dickinson & Company of Franklin Lakes, New Jersey).

In some embodiments, a fluid pathway of a blood collection system, which may include one or more of the blood sample access device 124, the fluid pathway within the IV device assembly 100 (which may include a lumen 102), and the VAD (which may include the catheter assembly 128 and/or an extension tube), may include an entirety of a blood collection pathway through which blood flows after leaving the blood vessel and into the blood collection device 124 during blood collection. The system geometric factor $G_{fs}$ for the fluid pathway of the blood collection system can be determined in similar fashion as the $G_f$ value of the lumen 102 as described earlier. In some embodiments, the system geometric factor $G_{fs}$ may be equal to or more than 7.34E+06 (1/in$^3$). In some embodiments, $G_{fs}$ may include another value. In some embodiments, the system geometric factor $G_{fs}$ may be equal to or more than 7.34E+06 (1/in$^3$) when the translation handle 114 is moved to a distal end of the IV device assembly 100. In some embodiments, the system geometric factor $G_{fs}$ may be 7.34E+06 (1/in$^3$) plus or minus 10 percent, plus or minus 25 percent, plus or minus 50 percent, or plus or minus 75 percent. In some embodiments, $G_{fs}$ may include another value, which may be selected based on a gauge and/or length of the catheter.

FIG. 4 also illustrates the interconnection between the lumen 102 and the grip 116, according to some embodiments. In this example, the grip 116 may be used as a fluidic path with a fluid bore formed therethrough. In some embodiments, the grip 116 may include a number of threads that interface with threads of the blood sample access device 124 so that they may be mechanically and fluidically coupled together. In other embodiments, the lumen 102 may be passed through a mechanical bore formed through the grip 116 and the grip 116 may be coupled to the exterior surface of the lumen 102 using an adhesive or other type of coupling mechanism. In some embodiments, the fluidic path of the lumen 102 may fluidically couple to the blood sample access device 124 to the funnel coupler channel 140 in the funnel coupler 106. In some embodiments, the portion of the IV device assembly 100 between the funnel coupler 106 and the grip 116 may be flexible so that movement of the IV device assembly 100 does not disturb the placement of a VAD coupled to the IV device assembly 100 via the VAD coupler 104.

Again, in some embodiments, the collapsible sleeve 110 may include a coil spring (not illustrated). The coil spring may expand the collapsible sleeve 110 to the state illustrated in FIG. 4 and may bias the translation handle 114 to a proximal end of the IV device assembly 100. In this state, the patency instrument 112 may be left in an undeployed state until the clinician translates the translation handle 114 towards a distal end of the IV device assembly 100.

FIG. 5 a perspective view of an IV device assembly 100 according to some embodiments of the present disclosure. In FIG. 5, the translation handle 114 has been translated a distance towards the distal end of the IV device assembly 100, according to some embodiments. By translating the translation handle 114 towards the distal end of the IV device assembly 100, a number of changes may occur to the IV device assembly 100. For example, the collapsible sleeve 110 may be collapsed and compacted between the translation handle 114 and the funnel coupler 106. As described in the present disclosure, the patency instrument 112 may also be passed through the channel 118 formed in the translation handle 114 and passed through the funnel coupler 106 and VAD coupler 104. This extends the patency instrument 112 out our the VAD coupler 104 and, when coupled, into the fluidic paths formed in a VAD coupled to the IV device assembly 100. The translation location of the translation handle 114 as illustrated in FIG. 5 may be an intermediate position such that the translation handle 114 may be passed further down towards and closer to the funnel coupler 106. In some embodiments, the translation handle 114 slides along the lumen 102 with the lumen 102 passing through a lumen bore formed through the translation handle 114.

In some embodiments, by extending the patency instrument 112 in this manner, the clinician may check the patency of the VAD coupled to the IV device assembly 100. In some embodiments, the extension of the patency instrument 112 and its porous distal end 138 into the VAD may move or push away anything that might occlude the catheter of the VAD during a blood draw. The material that may occlude the fluidic paths within the VAD may include fibrin material, thrombosis, or even a vein wall. In some embodiments, the patency instrument 112 may be stiff enough to open a valve downstream of the IV device assembly 100 to allow backflow into the catheter.

FIG. 6 is a front elevation view of an IV device assembly 100 according to some embodiments of the present disclosure. In some embodiments, the collapsible sleeve 110 is collapsed between the translation handle 114 and the funnel coupler 106 to extend the patency instrument 112 almost to a maximum or increased length. In these and other embodiments, the lumen 102 may include a number of measurement indicators 142 placed along the length of the lumen 102. The indicators may be physical markings that indicate to the clinician the distance that the patency instrument 112 has traveled out of the VAD coupler 104 and into the VAD coupled to the IV device assembly 100. Any number of measurement indicators 142 may be marked along the lumen 102 between the patency instrument 112 and the funnel coupler 106 and the present disclosure contemplates that these measurements may be in any imperial or metric increments. During operation, the clinician may determine the length of the fluidic paths within the VAD coupled to the IV device assembly 100 and cause the translation handle 114 to be translated towards the distal end of the IV device assembly 100 according to that length by using the measurement indicators 142 printed or marked on the lumen 102. This may allow the clinician to accommodate for shorter fluidic path lengths within a variety of VADs so that the patency instrument 112 is not extended into and out of the VAD and into, for example, a wall of the blood vessel thereby causing damage to the blood vessel. Because the IV device assembly 100 remains flexible relative to the VAD coupler 104, when the IV device assembly 100 is coupled to a VAD, the clinician will not dislodge or otherwise interfere with the placement of the VAD into the patient's arm while manipulating the translation handle 114. This prevents damage to the patient's body during the patency checking and during a blood draw to the blood sample access device 124.

Figure 7:
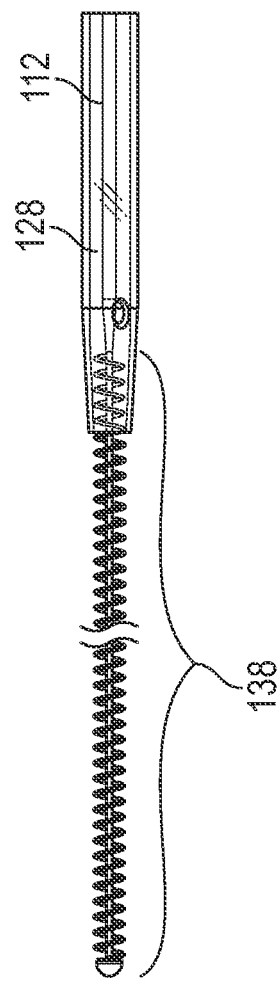
FIG. 7 is a front elevation view of a patency instrument according to some embodiments of the present disclosure.

FIG. 7 is a front elevation view of a patency instrument 112 according to some embodiments of the present disclosure. In some embodiments, as illustrated, for example, in FIG. 7, the patency instrument 112 may extend through the catheter assembly 128 mechanically and fluidically coupled to the IV device assembly 100 of, for example, FIGS. 1 and 2. The patency instrument 112 is illustrated to be extended slightly past a distal end of the catheter assembly 128 due to the clinician passing the translation handle 114 towards a distal end of the IV device assembly 100 as described in the present disclosure. As also described in the present disclosure, the distal end of the patency instrument 112 may include a porous distal end 138. In these embodiments, the patency instrument 112 may be necked down to a smaller diameter and the porous distal end 138 may include a coil winding around the smaller diameter portion of the patency instrument 112. The coil winding is merely one example of what the porous distal end 138 may consist of and the present disclosure contemplates that other porous distal end 138 material may be used.

Additionally, the present disclosure contemplates that certain sensors may be placed within the coil windings or at the very distal end of the patency instrument 112 so that certain physiological characteristics of the patient may be monitored such as blood pressure, pH of the patient's blood, blood chemistry, peripheral capillary oxygen saturation (SPO2) levels, blood flow rate, heartbeat, and temperature, among others.

The coil windings illustrated at the porous distal end 138 of the patency instrument 112 are depicted as having a constant pitch across the entire length of the porous distal end 138. However, the present disclosure contemplates that the pitch of the coil windings may vary along the length of the porous distal end 138. The variance in pitch may be a repeating variance, a constant variance or a random variance in order to fit certain patency-checking qualities of the patency instrument 112.

Figure 8:
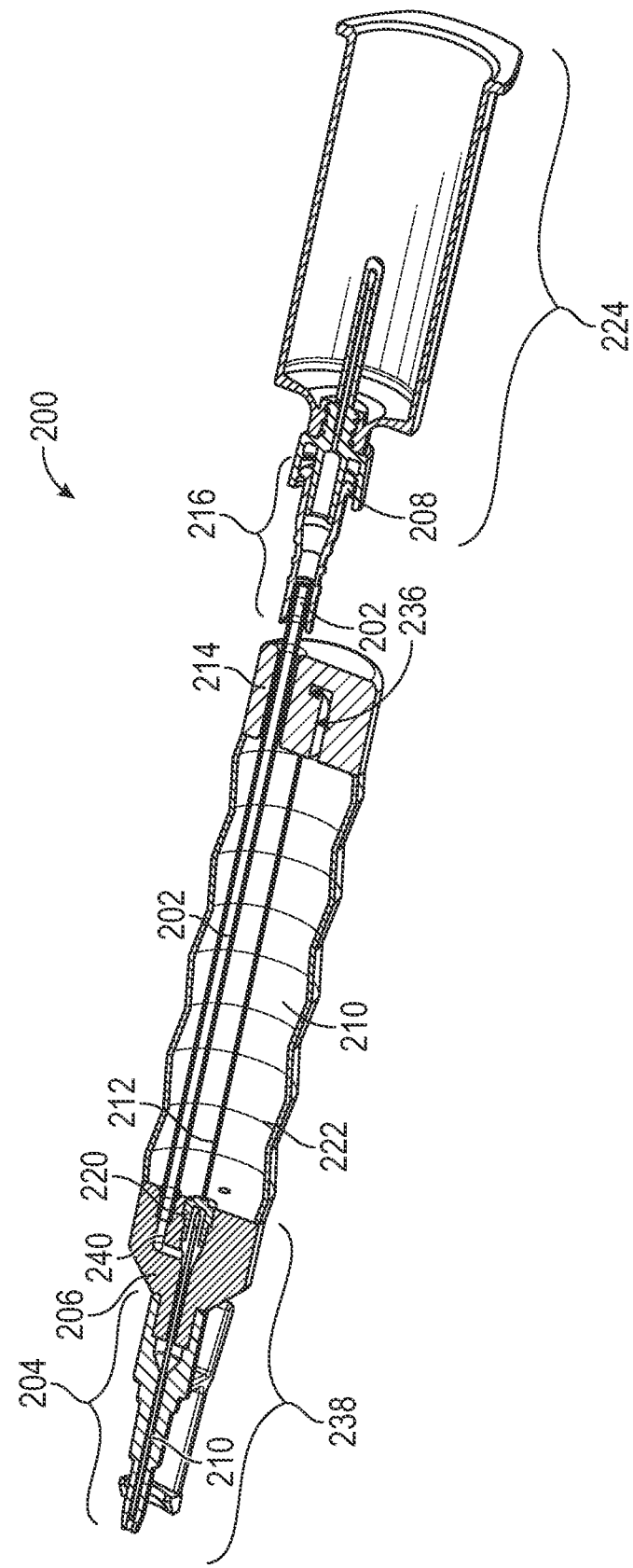
FIG. 8 is a perspective, section view of an IV device assembly, according to some embodiments of the present disclosure.

FIG. 8 is a perspective, section view of an IV device assembly 200 according to some embodiments of the present disclosure. The IV device assembly 200 illustrated in FIG. 8 is similar to that illustrated in FIG. 4 and includes a lumen 202 fluidically coupling a blood sample access device 224 to a funnel coupler 206. As described in the present disclosure, a proximal end of the lumen 202 may be coupled to the blood sample access device 224 via an IV device assembly coupler 208. Additionally, similar to FIG. 4, the IV device assembly 200 may include a collapsible sleeve 210 that is formed coaxially around a first portion of the lumen 202 and mechanically coupled to the funnel coupler 206. During operation of the IV device assembly 200, a clinician may grasp the grip 216 with one hand or multiple fingers and translate the translation handle 214 along the length of the translation handle 214 towards a distal end of the IV device assembly 200 with another hand or other fingers. In some embodiments, the ergonomics that define the shape of the grip 216 may be such that the grip 216 and translation handle 214 is operated with a single hand. In some embodiments, the collapsible sleeve 210 may include a coiled spring 222 formed therein to cause the collapsible sleeve 210 to be extended (e.g., as illustrated in FIG. 1) when a force is not applied to the translation handle 214 towards a distal end of the IV device assembly 200. In some embodiments, the coiled spring 222 may be biased to return to the non-deployed states as illustrated in FIG. 1.

Similar to FIG. 4, a distal end of the patency instrument 212 may include a porous distal end 238. The porous distal end 238 may be made porous by, in some embodiments, coupling a spring winding around the distal end of the guidewire that forms the patency instrument 212.

In FIG. 8, however, the patency instrument 212 is illustrated to be a single pass patency instrument 212. That is, instead of the first end of the patency instrument 212 being anchored to the funnel coupler 206, the first end of the patency instrument 212 is anchored to the translation handle 214 at a patency instrument anchor 236. Accordingly, the distance the patency instrument 212 may be translated out of the IV device assembly 200 is roughly half that as illustrated in FIG. 4. Instead, the distance the patency instrument 212 may be translated out of the IV device assembly 200 may roughly be equal to the length between a proximal side of the funnel coupler 206 and the distal side of translation handle 214.

As described in the present disclosure, a funnel coupler channel 240 is illustrated formed through the funnel coupler 206. As described in the present disclosure, the fluid channel of the lumen 202 is formed at the funnel coupler 206 at a location offset from the fluidic channel of the VAD coupler 204. In order to fluidically couple the lumen 202 to the fluidic channel formed through the VAD coupler 204, the funnel coupler 206 may have a funnel coupler channel 240 formed therethrough in order to fluidically connect these two fluidic paths.

The IV device assembly 200 illustrated in FIG. 8 may be used in connection with those VADs whose fluidic path is relatively short compared to those used with the IV device assembly 100 depicted in FIG. 4. In some embodiments, the distance between the distal end of the VAD coupled to the IV device assembly 200 may be shorter than that illustrated in FIG. 4 due to the lack of any intervening lengths of extension tubing placed between the VAD coupler 204 and the catheter assembly 128 of the VAD illustrated in FIG. 2. In some embodiments, the size of the VAD coupled to the IV device assembly 200 via the VAD coupler 204 may be smaller such that the use of a double lengthened patency instrument 112 as illustrated in FIG. 4 may be unnecessary.

In some embodiments, the IV device assembly 200 of FIG. 8 may prevent the need to form the channel 118 (FIG. 1) within the translation handle 214 because the patency instrument 212 does not pass through the translation handle 214. Instead, movement of the translation handle 214 towards the distal end of the IV device assembly 200 cause the patency instrument 212 to exit the VAD coupler 204.

FIG. 9 is a perspective view of an IV device assembly 300 according to some embodiments of the present disclosure. In these embodiments, the IV device assembly 300 may include a funnel coupler 306 that is mechanically and fluidically coupled to an indwelling catheter 346. The indwelling catheter 346 may include a catheter/needle assembly 328 that is fluidically and mechanically coupled to the funnel coupler 306.

In some embodiments, the IV device assembly 300 may include a patency instrument 312 that is anchored to the IV device assembly 300 at a patency instrument anchor 336. In some embodiments, the patency instrument 312 may then be passed through a channel (not illustrated) formed through the translation handle 314 and passed into the funnel coupler 306. As such, the patency instrument 312 is illustrated to be a double passing patency instrument 312 as descried in the present disclosure.

FIG. 9 also illustrates that the grip 316 is formed alongside the IV device assembly coupler 308, according to some embodiments. In these embodiments, the space occupied by the grip 316 and the IV device assembly coupler 308 is reduced through the use of the grip 316 formed on the sides of the IV device assembly coupler 308.

FIG. 9 also illustrates a lumen 302 that is also offset from a fluidic path formed in the indwelling catheter 346, according to some embodiments. Although the components of the IV device assembly are relatively more rigid than those illustrated and described in connection with FIG. 1, the length of the IV device assembly 300 in FIG. 9 may be reduced eliminating the materials used and the bulk of the IV device assembly 300.

Figure 10B:
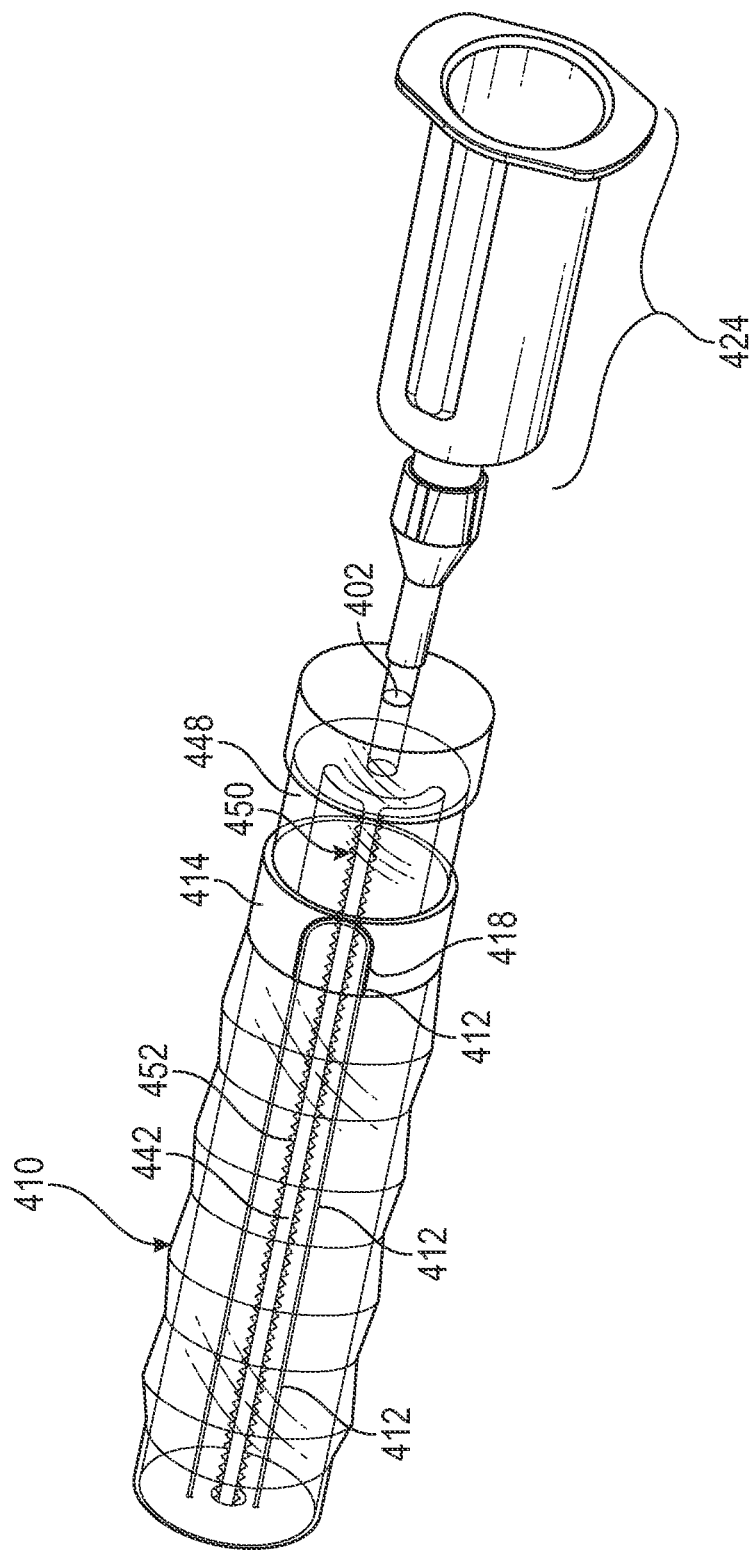
FIG. 10B is a perspective view of a rigid or semi-rigid IV device assembly, according to some embodiments of the present disclosure.

FIG. 10A is a perspective, section view of an IV device assembly 400 according to some embodiments of the present disclosure. FIG. 10B is a perspective view of the IV device assembly 400 according to some embodiments of the present disclosure. The IV device assembly 400 of FIGS. 10A and 10B may be rigid or semi-rigid due to the use of a relatively more rigid solid lumen 448 than the lumen described in connection with FIG. 1. FIG. 10A illustrates a lumen 402 that is offset relative to the fluidic path formed in the VAD coupler 404 with the mechanical path of the patency instrument 412 being aligned with the fluidic path formed in the VAD coupler 404. FIG. 10B illustrates a patency instrument 412 that is offset relative to the fluidic path formed in the VAD coupler 404 with the fluidic path of the lumen 402 being aligned with the fluidic path formed in the VAD coupler 404. The present specification contemplates that any of these paths (e.g., mechanical path of the patency instrument 412 and fluidic path of the lumen 402) may be either aligned with or offset from the fluidic path formed in the VAD coupler 404.

In some embodiments, the solid lumen 448 may be made of a material that maintains the rigidity of the lumen 402 formed therethrough. In these embodiments, the lumen 402 may be fluidically coupled to a blood sample access device 424 via an IV device assembly coupler 408 similar to other embodiments described in the present disclosure. In some embodiments, the solid lumen 448 may also include a channel 442 formed along a length of the solid lumen 448.

In an embodiment, the channel 442 may be used to house the patency instrument 412 therein for translation through the funnel coupler 406, into the VAD coupler 404, and out of the IV device assembly 400. In these embodiments, the solid lumen 448 may include a channel 442 formed therein to allow the patency instrument 412 to pass from a patency instrument anchor 436 at the first end of the patency instrument 412 through a channel 418 formed in a portion of the translation handle 414 mechanically coupled to the channel 442 and into the VAD coupler 404 via a bore formed therein. In some embodiments, the channel 442 may be quarter-moon shaped.

In the embodiments described in the present disclosure, the translation handle 414 may include a curved piece formed within the channel 442 such that the channel 418 for the patency instrument 412 may be formed therein for the patency instrument 412 pass through. This channel 418 used to pass the patency instrument 412 through the translation handle 414 may be formed in the part of the translation handle 414 that is placed within the channel 442. In some embodiments, during operation, as the translation handle 414 is translated towards the distal end of the IV device assembly 400, the patency instrument 412 is passed through the channel 418 and into the VAD coupler 404 to extend the patency instrument 412 into a VAD coupled to the IV device assembly 400 via the VAD coupler 404.

In some embodiments, the patency instrument 412 may include a porous distal end 438. The porous distal end 438 may be made porous by, in some embodiments, coupling a spring winding around the distal end of the guidewire that forms the patency instrument 412. The spring winding may be in the form of a fixed coil, a variable coil, a repeating variable coil, and open-ended extended coil, among other configurations. In some embodiments, the spring winding of the porous distal end 438 may be capped with a knob. In some embodiments, the length of the porous distal end 438 may vary and may be as long as or shorter than the distance between a distal end of the fluidic channel formed in the VAD coupler 404 to the distal end of a seal (not illustrated) formed in the VAD coupler 404 used to seal the patency instrument 412 bore from the fluidic paths within the VAD coupler 404 and the solid lumen 448. In these embodiments, the diameter of the bore through the seal may be smaller than the diameter of the porous distal end 438 and the porous distal end 438 may be prevented from entering the bore formed through the seal.

In some embodiments, the translation handle 414 may include a series of locking teeth 452 that interfaces with channel locking teeth 450 formed at an opening leading to the channel 442. During operation, the translation handle 414 may be pinched by the clinician in order to disengage the locking teeth 452 formed on the translation handle 414 from those channel locking teeth 450 formed on the opening leading to the channel 442. As such, the clinician may secure the translation handle 414 at any distance along the solid lumen 448 so that any portion or length of the patency instrument 412 extends out of the VAD coupler 404 and into, for example, a PIVC coupled to the VAD coupler 404.

In another embodiment, the translation handle 414 may include a spring mechanism (not illustrated) that is biased against the walls of the opening leading to the channel 442, which may include a quarter-moon shape, when pressure is not applied to the translation handle 414. When a clinician or other HCP applies a pinching force against the translation handle 414 at a location on the translation handle 414, the pressure may compress the biased spring mechanism and release the translation handle 414 to slide along the longitudinal axis of the lumen 448, which may be rigid or semi-rigid. Again, by doing so, the clinician may secure the translation handle 414 at any distance along the solid lumen 448 so that any portion or length of the patency instrument 412 extends out of the VAD coupler 404 and into, for example, a PIVC coupled to the VAD coupler 404.

In the embodiment illustrated in FIG. 10B, a collapsible sleeve 410 may be formed around the solid lumen 448. In an embodiment, the collapsible sleeve 410 may be mechanically coupled to a distal side of the translation handle 414. Additionally, the collapsible sleeve 410 may be coupled to a distal end of the solid lumen 448. In these embodiments, the collapsible sleeve 410 may prevent contaminants from entering into the channel 442 during operation and coming into contact with a surface of the patency instrument 412.

Still further, the lumen 402 may be fluidically coupled to a blood sample access device 424 via an IV device assembly coupler 408 similar to other embodiments described in the present disclosure. In these embodiments, a blood sampling tube (not illustrated) may be inserted into the blood sample access device 424. In a specific embodiment, upon insertion of the blood sampling tube being inserted into the blood sample access device 424, a septum formed on the blood sampling tube may be pierced by a needle within the blood sample access device 424. Blood may then be allowed to flow into the blood sampling tube and a blood sample may be received.

Figure 10C:
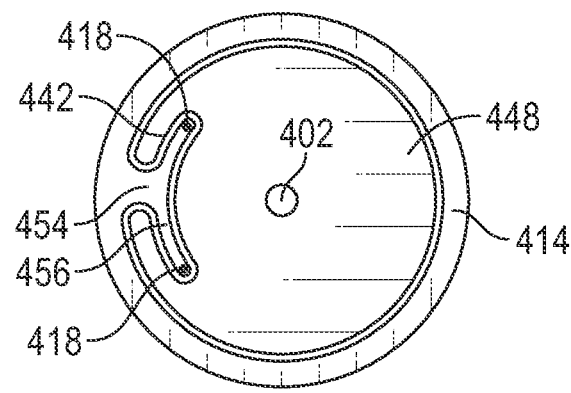
FIG. 10C is a side elevation view of a rigid or semi-rigid IV device assembly, according to some embodiments of the present disclosure.
Figure 10D:
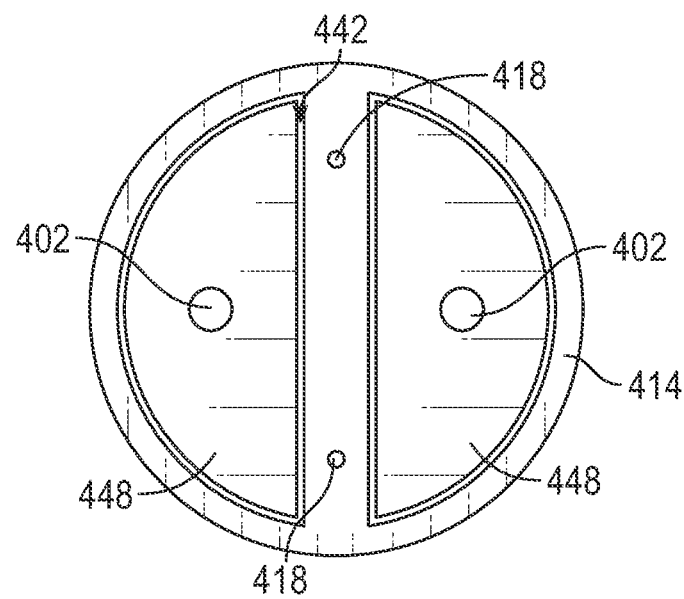
FIG. 10D is a side elevation view of a rigid or semi-rigid IV device assembly, according to some embodiments of the present disclosure.
Figure 10E:
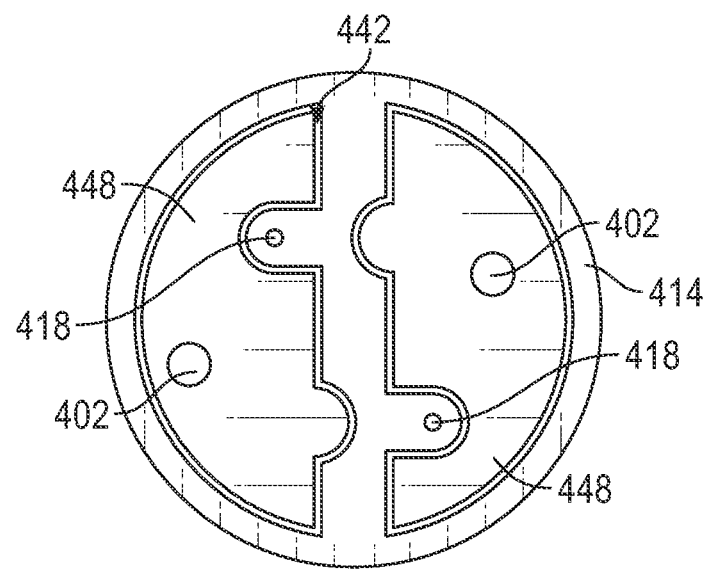
FIG. 10E is a side elevation view of a rigid or semi-rigid IV device assembly, according to some embodiments of the present disclosure.
Figure 10F:
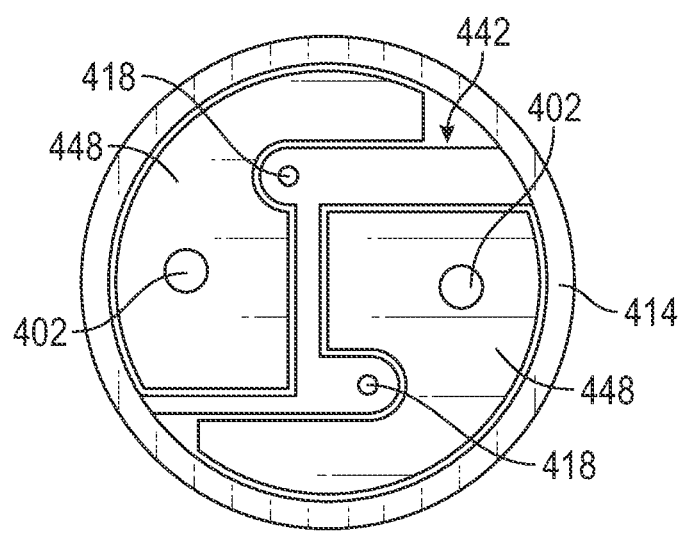
FIG. 10F is a side elevation view of a rigid or semi-rigid device assembly, according to some embodiments of the present disclosure.

FIG. 10C is a side elevation view of the IV device assembly 400 assembly, which may be rigid or semi-rigid, according to some embodiments of the present disclosure. FIG. 10D is a side elevation view of the IV device assembly 400 assembly, which may be rigid or semi-rigid, according to some embodiments of the present disclosure. FIG. 10E is a side elevation view of the IV device assembly 400, which may be rigid or semi-rigid, according to some embodiments of the present disclosure. FIG. 10F is a side elevation view of the IV device assembly 400, which may be rigid or semi-rigid, according to some embodiments of the present disclosure. Each of these views show a possible shape of a channel 442 formed through the rigid or semi-rigid solid lumen 448 as described in connection with FIGS. 10A and 10B.

FIG. 10C illustrates that the channel 442 is in the form of a quarter-moon as illustrated in FIG. 10B. In some embodiments, the lumen 402 may be centered with the fluidic path formed in the VAD coupler 404 as illustrated in FIG. 10A. In some embodiments, the lumen 402 may be offset relative to the fluidic path formed in the VAD coupler 404 as illustrated in FIG. 10A.

FIG. 10C also illustrates the translation handle 414 formed around the solid lumen 448. In this embodiment, the translation handle 414 includes a neck portion 454 and a crescent moon-shaped body 456. In this embodiment, the translation handle 414, the neck portion 454, and the crescent moon-shaped body 456 may be formed into a monolithic piece. Also illustrated in FIG. 10C is the channel 418 formed through the crescent moon-shaped body 456 of the translation handle 414. As described in the present disclosure, the patency instrument 412 may be passed through this channel 418 such that as the translation handle 414 is translated either distally or proximally along a longitudinal axis of the solid lumen 448 causes the patency instrument 412 to be extended from or retracted into the solid lumen 448, respectively. Although FIG. 10C illustrates that the channel 442 interfaces with the translation handle 414 via the crescent moon-shaped body 456 and neck portion 454, the present specification contemplates that any extension from the translation handle 414 may be used based on the shape and form of the solid lumen 448 so that a channel 418 may be formed therethrough and pass the patency instrument 412 therein as described.

FIG. 10D illustrates one or more lumens 402 may be formed through the solid lumen 448 to accommodate for one or more types of fluids to pass through the solid lumen 448 or a single fluid via the lumens 402, according to some embodiments. Additionally, in these embodiments, the channel 442 may be formed through the center of the solid lumen 448. In some embodiments, the patency instrument 412 may be passed through this channel 442 such that the patency instrument 412 passes into the lumen 402 at a location offset from the fluidic path formed through the VAD coupler 404. Additionally, in some embodiments, the lumens 402 may be offset from the fluidic path formed through the VAD coupler 404. In FIG. 10D, the translation handle 414 includes an arm that intersects the channel 442 formed through the solid lumen 448. Again, the arm includes a channel 418 through which the patency instrument 412 may pass as described in the present disclosure.

FIG. 10E illustrates that the solid lumen 448 may also include one or more lumens 402, according to some embodiments. The lumens 402 may accommodate for one or more types of fluids to pass through the solid lumen 448 or a single fluid via the lumens 402. The lumens 402 are illustrated to also be offset from the fluidic path formed through the VAD coupler 404. FIG. 10E also illustrates that the channel 442 may be formed through the solid lumen 448, according to some embodiments. In these embodiments, the channel 442 may include a number of dedicated channel portions through which the patency instrument 412 may pass while a number of mating bumps may be used to maintain an alignment of the patency instrument 412 as it passes through the channel 442. In FIG. 10E, the translation handle 414 includes an arm that intersects the channel 442 formed through the solid lumen 448. In contrast to FIG. 10D, the arm snakes through the channel 442 in a similar shape to the channel 442. Again, the arm includes a channel 418 through which the patency instrument 412 may pass as described in the present disclosure.

FIG. 10F illustrates that the solid lumen 448 include one or more lumens 402. The lumens 402 may accommodate for one or more types of fluids to pass through the solid lumen 448 or a single fluid via the lumens 402. The lumens 402 are illustrated to also be offset from the fluidic path formed through the VAD coupler 404. FIG. 10F also illustrates the channel 442 that may be snake-shaped. In this example, the channel 442 may include a number of dedicated channel portions through which the patency instrument 412 may pass. In FIG. 10F, the translation handle 414 includes an arm that intersects the channel 442 formed through the solid lumen 448. In contrast to FIG. 10D, the arm snakes through the channel 442 in a similar shape to the channel 442. Again, the arm includes a channel 418 through which the patency instrument 412 may pass as described in the present disclosure.

In each of FIGS. 10C through 10F, the translation handle 414 may be wrapped around the outer surface of the solid lumen 448 and interface with the solid lumen 448 and patency instrument 412 as described in connection with FIGS. 10A and 10B. The translation handle 414 may in some embodiments, be made of an elastically pliable material that returns to its original shape when the clinician is not applying a pinching force against the translation handle 414 in order to translate the translation handle 414 towards a distal end of the IV device assembly 400.

Figure 11:
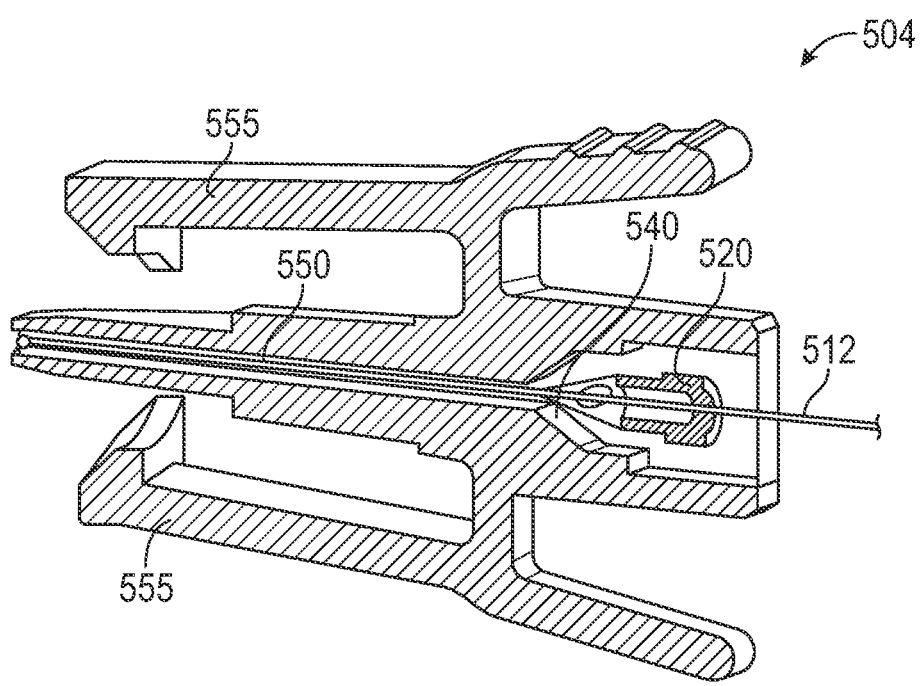
FIG. 11 is a perspective view of a vascular access device (VAD) coupler assembly, according to some embodiments of the present disclosure.

FIG. 11 is a perspective view of a VAD coupler 504 assembly, according to some embodiments of the present disclosure. The VAD coupler 504 may be, in some embodiments, a combination of a VAD coupler 104 and funnel coupler 106 as illustrated in FIG. 1.

As described in the present disclosure, the patency instrument 512 may be passed through the VAD coupler 504 for a distance. The embodiment illustrated in FIG. 11, the patency instrument 512 may extend up to a distal end of the VAD coupler 504. Additionally, the distal end of the patency instrument 512 may be a porous distal end.

The VAD coupler 504 may further include a coupler channel 540. The coupler channel 540 may funnel the output from one or more lumens fluidically coupled to the VAD coupler 504 to the fluid channel 550. The coupler channel 540 may receive fluid from one or more lumens as described in connection with FIG. 1.

The VAD coupler 504 may further include a seal 520. The seal 520 may prevent fluids within coupler channel 540 and fluid channel 550 from exiting out of a location where the patency instrument 512 interfaces with the VAD coupler 504. The seal may prevent those fluids from entering into, for example, the collapsible sleeve described in connection with FIG. 1.

The VAD coupler 504 may further include a number of coupler grip arms 555. In this specific example of a VAD coupler 504, the coupler grip arms 555 may be used to mechanically secure the VAD coupler 504 to a VAD thereby fluidically coupling the fluid channel 550 to a fluidic path formed in the coupled VAD. Although FIG. 11 illustrates a specific type of VAD coupler 504, the present disclosure contemplates that any type of coupler may be used such as a blunt cannula snap connection (e.g., VAD coupler 504), a threaded male luer coupler, a slip luer coupler, and a threaded male luer with a removably attached blunt cannula snap connector, among others.

The IV device assembly described in the present disclosure may provide for an integrated extension set in the form of the present IV device assembly with an optimized fluidic resistance that includes a patency improving guidewire instrument that is relatively less traumatic on a patient's blood vessel. The presently described present IV device assembly include a patency instrument that may be operated using a single hand. The present IV device assembly described in the present disclosure may be more compact than other extension sets may combine the patency checking processes with blood sampling processes via use of the blood sample access device for improved workflow and reduce steps and processes in patency checking and blood sampling. Due to the form and components used in the present IV device assembly, the amount of waste may be reduced and the amount of waste produced.

All examples and conditional language recited in the present disclosure are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An intravenous (IV) device assembly, comprising:
a collapsible sleeve defining a chamber;
a coupler comprising a passageway provided at a distal end of the chamber;
a vascular access device (VAD) coupler having a passageway in fluid communication with the passageway of the coupler;
a solid core provided within the chamber, the solid core defining a lumen channel and a patency instrument channel;
a lumen passing through the lumen channel of the solid core, the lumen in fluid communication with the passageway of the coupler;
a patency instrument extending through the patency instrument channel of the solid core; and
a translation handle surrounding a portion of the solid core,
wherein the translation handle is movable along the solid core to translate the patency instrument through the patency instrument channel, through the passageway of the coupler, and out of a distal end of the VAD coupler.

2. The intravenous (IV) device assembly of claim 1, wherein the translation handle comprises an inwardly extending protrusion received within the patency instrument channel of the solid core, and the protrusion comprises a channel through which the patency instrument passes.

3. The intravenous (IV) device assembly of claim 2, wherein the protrusion has a shape substantially corresponding to a shape of the patency instrument channel.

4. The intravenous (IV) device assembly of claim 2, wherein the protrusion comprises a channel portion defining the channel through which the patency instrument passes, and the patency channel of the solid core comprises a notch that receives the channel portion of the protrusion.

5. The intravenous (IV) device assembly of claim 4, wherein the protrusion comprises two channel portions and a connecting member connecting the two channel portions.

6. The intravenous (IV) device assembly of claim 5, wherein the connecting member extends from opposite sides of the translation handle.

7. The intravenous (IV) device assembly of claim 5, wherein the channel portions extend from opposite sides of the translation handle.

8. The intravenous (IV) device assembly of claim 2, wherein the protrusion comprises an alignment notch, and the patency channel of the solid core comprises an alignment portion that is received in the alignment notch of the protrusion.

9. The intravenous (IV) device assembly of claim 1, wherein the lumen is offset from the passageway of the VAD coupler and the patency instrument is aligned with the passageway of the VAD coupler.

10. The intravenous (IV) device assembly of claim 1, wherein the lumen is aligned with the passageway of the VAD coupler, and the patency instrument is offset from the passageway of the VAD coupler.

11. The intravenous (IV) device assembly of claim 1, wherein the intravenous (IV) device assembly comprises more than one lumen, each lumen passing through a lumen channel in the solid core.

12. The intravenous (IV) device assembly of claim 1, wherein the patency instrument channel substantially bisects the solid core.

13. The intravenous (IV) device assembly of claim 12, wherein the intravenous (IV) device assembly comprises two lumens, each lumen passes through a lumen channel in the solid core, and the lumen channels are on opposite sides of the patency instrument channel.

14. The intravenous (IV) device assembly of claim 1, further comprising a fixed grip formed around the lumen.

15. The intravenous (IV) device assembly of claim 1, wherein a first end of the patency instrument is mechanically coupled to the coupler and a second end of the patency instrument extends into the VAD coupler.

16. The intravenous (IV) device assembly of claim 1, where in the patency instrument is a guidewire.

17. The intravenous (IV) device assembly of claim 1, wherein the collapsible sleeve is mechanically coupled to the coupler.

18. The intravenous (IV) device assembly of claim 1, further comprising an intravenous (IV) device assembly coupler at a proximal end of the lumen.

19. The intravenous (IV) device assembly of claim 17, further comprising a catheter coupled to the VAD coupler, and a blood sample access device mechanically coupled to the intravenous (IV) device assembly coupler.

* * * * *